(12) United States Patent
Neto

(10) Patent No.: US 9,974,813 B1
(45) Date of Patent: May 22, 2018

(54) THERAPEUTIC SERUM OBTAINED FROM CO-CULTURED CELLS

(71) Applicant: Serucell Corporation, Palo Alto, CA (US)

(72) Inventor: Walter De Paula Neto, Lavalette, WV (US)

(73) Assignee: SERUCELL CORPORATION, Palo Alto, CA (US)

(*) Notice: Subject to any disclaimer, the term of this patent is extended or adjusted under 35 U.S.C. 154(b) by 0 days. days.

(21) Appl. No.: 15/700,895

(22) Filed: Sep. 11, 2017

Related U.S. Application Data

(63) Continuation-in-part of application No. 14/597,796, filed on Jan. 15, 2015, now Pat. No. 9,907,745.

(60) Provisional application No. 61/927,674, filed on Jan. 15, 2014.

(51) Int. Cl.
| | |
|---|---|
| *C12P 1/00* | (2006.01) |
| *A61K 35/36* | (2015.01) |
| *C12N 5/077* | (2010.01) |
| *C12N 5/071* | (2010.01) |
| *A61K 35/35* | (2015.01) |
| *A61K 8/98* | (2006.01) |
| *A61Q 19/00* | (2006.01) |

(52) U.S. Cl.
CPC .............. *A61K 35/36* (2013.01); *A61K 8/981* (2013.01); *A61K 8/985* (2013.01); *A61K 35/35* (2013.01); *A61Q 19/00* (2013.01); *C12N 5/0629* (2013.01); *C12N 5/0656* (2013.01); *C12N 2501/10* (2013.01); *C12N 2502/094* (2013.01); *C12N 2502/1323* (2013.01)

(58) Field of Classification Search
CPC ......................................................... C12P 1/00
See application file for complete search history.

(56) References Cited

U.S. PATENT DOCUMENTS

| | | | |
|---|---|---|---|
| 4,016,036 | A | 4/1977 | Green et al. |
| 5,561,107 | A | 10/1996 | Jaynes et al. |
| 6,191,110 | B1 | 2/2001 | Jaynes et al. |
| 7,118,746 | B1 | 10/2006 | Naughton et al. |
| 8,138,147 | B2 | 3/2012 | Naughton et al. |
| 8,246,969 | B2 | 8/2012 | Engles et al. |
| 8,246,971 | B2 | 8/2012 | Engles et al. |
| 8,268,336 | B2 | 9/2012 | Engles et al. |
| 8,361,485 | B2 | 1/2013 | Naughton et al. |
| 8,476,231 | B2 | 7/2013 | Naughton et al. |
| 8,518,422 | B2 | 8/2013 | Monks et al. |
| 2001/0048917 | A1 | 12/2001 | Hoeffler et al. |
| 2004/0116356 | A1 | 6/2004 | Malik |
| 2006/0165667 | A1* | 7/2006 | Laughlin ................ A61K 35/28 424/93.21 |
| 2009/0202654 | A1 | 8/2009 | Nixon |
| 2011/0177015 | A1 | 7/2011 | Friedlander |
| 2015/0196484 | A1 | 7/2015 | Neto |

FOREIGN PATENT DOCUMENTS

| | | |
|---|---|---|
| CA | 2367281 | 9/1999 |
| EP | 1375646 | 1/2004 |
| WO | 2006014089 | 2/2006 |
| WO | 2007005659 | 1/2007 |
| WO | 2010086754 | 8/2010 |
| WO | 2011138687 | 11/2011 |

OTHER PUBLICATIONS

Berse et al. (1999) Clin. Exp. Immunol. 115: 176-182, U.S. Appl. No. 14/597,796.
Garner(1998) Plastic and Reconstructive Surgery, vol. 102, No. 1, 135-139, U.S. Appl. No. 14/597,796.
Ghaffari et al. (2009) J. Invest. Dermatol. vol. 129, 340-347, U.S. Appl. No. 14/597,796.
Hawley-Nelson (1980) J. Invest. Dermatol. 75: 176-182, U.S. Appl. No. 14/597,796.
Kubo et al. (1984) J. Invest. Dermatol. 82: 580-586, U.S. Appl. No. 14/597,796.
Li et al. (1010) FEBS J. 277: 3688-3698, U.S. Appl. No. 14/597,796.
Lim et al. (2002) Am. J. Physiol. Cell Physiol. 283: C212-C222, U.S. Appl. No. 14/597,796.
Wong et al. (2007) British Journal of Dermatology 156: 1149-1155, U.S. Appl. No. 14/597,796.
Notice of Allowance from U.S. Appl. No. 14/597,796 dated Dec. 28, 2017; 9 pages.

* cited by examiner

*Primary Examiner* — Rosanne Kosson
(74) *Attorney, Agent, or Firm* — Andrew D. Wright; Roberts Mlotkowski Safran Cole & Calderon, P.C.

(57) ABSTRACT

A therapeutic serum suitable for inclusion in a cosmetic preparation may be produced by stressing a co-culture including proliferative cells. The co-culture of cells may be obtained by first establishing a monolayer of cells on a surface. After a monolayer of first culture is established, a second culture comprising more resilient and/or aggressive cells may be over-seeded on the monolayer and established. Additional cultures comprising increasingly dominant cells may then be over-seeded and established until a monolayer having the desired population of cells is obtained. The monolayer is then stressed to obtain a serum by conditioning a collection medium. The obtained serum may be combined with a suitable cosmetic base to provide a cosmetic preparation.

10 Claims, No Drawings

THERAPEUTIC SERUM OBTAINED FROM CO-CULTURED CELLS

FIELD

A therapeutic serum suitable for inclusion in a cosmetic preparation, a method of obtaining such serum and cosmetic preparations containing such serum are provided.

BACKGROUND

Skin is an essential multilayer organ. Providing a barrier against pathogens and toxins, as well as synthesizing nutrients such as vitamin D, skin is essential for maintaining an individual's physical health. The integrity of skin is also essential for maintaining one's psychological health. Skin is the most prominent part of an individual's body. Blemishes, scars, wrinkles and perceived imperfections can diminish an individual's self-confidence. Maintaining physical and psychological health, therefore, requires maintaining healthy skin.

Healthy skin comprises layers of different cells supported by a scaffolding of proteins called the extracellular matrix. The extracellular matrix supporting the skin comprises various proteins such as collagen, fibronectin and laminin. These and other structural proteins intertwine and communicate to form the structural and dynamic three-dimensional scaffolding providing skin with its strength and resilience. Cells forming the various layers of skin adhere to the extracellular matrix, and rely on both structural and biologically active signal relaying molecules within the matrix to maintain proper function. During wound healing, cells also use the extracellular matrix as a bridge to migrate into and close wounds. Providing support and pathways for healing, the extracellular matrix is an important structural and biologically active component of healthy skin. As an individual ages, however, the extracellular matrix changes and becomes weakened, leading to the appearance of wrinkles, blemishes and decreased healing.

The extracellular matrix is manufactured and maintained primarily by fibroblasts beneath the skin's surface. Manufacturing and maintaining the biological activity of the extracellular matrix, healthy fibroblasts are essential for healthy skin. Above the fibroblasts, on top of the extracellular matrix, are keratinocytes forming the epidermis. Forming the epidermis, the outer layer of skin, healthy keratinocytes are also essential for the appearance and integrity of skin. Accordingly, maintaining healthy skin from its base to its surface requires promoting the health of different cells throughout the layers of skins.

SUMMARY

A serum collected from a growing culture of skin cells may provide the various proteins, cytokines, glycans, hormones and other molecular factors necessary for maintaining a healthy extracellular matrix and epidermis as to promote wound healing, maintain the integrity of skin and/or lessen blemishes, such as wrinkles and scars. Given that healthy skin comprises various cells, such as keratinocytes, fibroblasts, mesodermal cells, melanocytes, Merkel Cells, Langerhans cells, etc, collecting a serum from a growing culture comprising keratinocytes, fibroblasts, mesodermal cells, melanocytes, Merkel Cells, Langerhans cells and/or other skin cells would better match the complete needs of new and aging skin. However, different growth rates and/or nutrients requirements may complicate efforts to co-culture different cells. Fibroblasts, for instance, are much more resilient and have a more aggressive growth pattern than other skin cells, such as keratinocytes. Consequently, attempting to co-culture fibroblasts with keratinocytes and/or other skin cells can easily result in a culture dominated by fibroblasts. Being dominated by one type of cell over the other types, intercellular signaling, such as paracrine signaling, may be altered, diminished and/or lost. Having altered and/or diminished intercellular signaling, such a culture would be unlikely to produce a serum having all the proteins and/or other molecular factors necessary for healing and maintaining the health of wounded and/or aging skin. The composition of serum generated by a culture dominated by one type of cell may also be altered by the less dominant cells becoming senescent. Cells are more productive when they are actively proliferating. Additionally, cells in the proliferative phase produce different molecular factors then senescent cells. Having altered and/or diminished production of molecular factors, a co-culture comprising senescent cells may also be unlikely to produce a serum having all the proteins and/or other molecular factors necessary for healing and maintaining the health of wounded and/or aging skin. Preserving intercellular signaling and/or maintaining cells in the proliferative phase in a co-culture of skin cells, accordingly, may provide a therapeutic serum suitable for inclusion in cosmetic preparations.

The varied dominance of cells in co-culture can be overcome as to preserve intercellular signaling and/or maintain cells within the culture in their proliferative phases. Overcoming the dominance of some cells over others to obtain such a co-culture may be accomplished by seeding a surface first with a culture comprising less resilient and/or aggressive cells. For instance, the first seeded culture may comprise cells with slower doubling times than other cells to be cultured. When the co-culture is to comprise keratinocytes, keratinocytes may be established within a first seeded culture. After the first seeded culture has been established on the surface, cultures comprising a more dominant cell can be seeded on the surface to provide a co-culture. After the more dominant cells have been established, subsequent cultures can be seeded and established until a co-culture having the desired cells is obtained on the surface.

As to facilitate growth and establishment, a culture may be provided with a growth media comprising nutrients and growth factors. Growth factors are substances capable of stimulating healing, growth, cellular proliferation and/or cellular differentiation. Growth factors useful for facilitating growth and establishment of a culture of skin cells may include, but are not limited to, amino acids, such as L-Glutamine, hormones, such as hydrocortisone hemisuccinate, insulin and/or epinephrine, omega fatty acids, such as linoleic acid, vitamins, such as vitamin C, proteins, such as serum albumin, basic fibroblasts growth factor, epidermal growth factor, transforming growth factor, insulin, bovine pituitary extract and/or ApoTransferin, and/or glycerophospholipids, such as lecithin. Other growth factors may facilitate the growth of the other cells to be co-cultured. Accordingly, the growth factors added may be chosen to promote the growth and/or proliferation of a culture. If the culture includes keratinocytes, suitable growth factors may include, but are not limited to, bovine pituitary extract, L-glutamine, hydrocortisone hemisuccinate, transforming growth factor, insulin, epinephrine and/or ApoTransferrin.

The nutrients in the growth media provided to a culture need not be lavish or exceed the minimal nutrients required for survival and growth of the culture. As such, a basal medium and/or minimal essential medium can provide sufficient nutrients. Accordingly, the growth media provided to a culture may comprise growth factors combined with a basal medium and/or minimal essential medium. The growth media provided to a culture may include a balancing agent to buffer the media to a desired pH, such as, but not limited to, Earl's salts and/or 4-(2-hydroxyethyl)-1-piperazineethanesulfonic acid (HEPES).

Accordingly, when establishing a co-culture of cells, a first seeded culture may be provided with a growth media comprising nutrients and at least one growth factors as to facilitate establishment of the culture after being seeded onto a surface. The growth media provided to the first seeded culture may comprise a basal medium and/or minimal essential medium. The growth factors included within the growth media provided to the first seeded culture may include, but are not limited to, amino acids, such as L-Glutamine, hormones, such as hydrocortisone hemisuccinate, insulin and/or epinephrine, omega fatty acids, such as linoleic acid, vitamins, such as vitamin C, proteins, such as serum albumin, basic fibroblasts growth factor, epidermal growth factor, transforming growth factor, insulin, bovine pituitary extract and/or ApoTransferin, and/or glycerophospholipids, such as lecithin. If the first seeded culture includes keratinocytes, suitable growth factors may include, but are not limited to, bovine pituitary extract, L-glutamine, hydrocortisone hemisuccinate, transforming growth factor, insulin, epinephrine and/or ApoTransferrin.

It may be desirable to maintain cultures from which cells are to be harvested for co-culturing in a proliferative phase. Likewise, it may be desirable to maintain cells within seeded cultures in a proliferative phase. Maintaining cells within a culture in a proliferative phase may be accomplished by preventing the culture form achieving one-hundred percent confluence. Accordingly, as to maintain the cells of the first seeded culture in a proliferative phase, the first seeded culture should be grown to a monolayer of less than one-hundred percent confluence on the surface.

After the first culture has been established, a second culture comprising more resilient and/or aggressive cells may be over-seeded onto the surface. When a co-culture is to comprise fibroblasts, they may be included in the second and/or subsequent seeded cultures. If the co-culture is to comprise cells more resilient and/or aggressive then the first culture, but not as resilient and/or aggressive as other cells, the second culture may comprise cells having such an intermediate dominance. The cells of the final culture may include the most resilient and/or aggressive cells.

Achieving the desired cellular composition of the final co-culture may require seeding successive cultures onto previously established cultures at varying confluences. For example, if the final co-culture is to comprise a co-culture of a first cell, a second cell more dominant than the first cell, and third cell more dominant than the first and second cells, then it may be appropriate to first seed a culture of the least dominant cells onto the surface and grow the first seeded cells to approximately thirty-three percent confluence. A culture of the second cells may then be seeded onto the surface. The co-culture of the first and second cells may then be grown to approximately sixty-six percent confluence. Then a culture of the most dominant cells may be seeded onto the surface and the co-culture of the three cells grown to less than one-hundred percent confluence.

Likewise, if the final co-culture is to comprise a co-culture of two cells, with the second more dominant than the first, then it may be appropriate grow the first seeded culture of the non-dominant cells to approximately fifty percent confluence before seeding the second cells onto the surface.

The above examples are based upon situations in which subsequent seeded cultures comprise cells sufficiently more dominant than previously seeded cultures such that the growth of previously seeded cultures can be treated as halted, and that a final co-culture having equal amounts of each culture is desired. This may not be true for every co-culture to be produced. Accordingly, it may be advantageous to grow the first seeded culture and/or subsequent co-cultures to other confluences as to account for growth rates of previously seeded cultures with subsequently seeded cultures and/or the desired cellular composition of the final co-culture.

The cells of the second or other subsequent cultures seeded onto the surface having a monolayer of preceding cultures may be provided in suspension. The suspension may be acquired from one or more separately grown cultures. Such cultures may be grown on a surface and/or in suspension in the presence of a growth media including growth factors and nutrients. The nutrients provided in the growth media of the subsequent cultures and/or cultures from which cells to be seeded are harvested do not need to be lavish or exceed the minimal nutrients required for survival and growth of the culture. As such, a basal medium and/or minimal essential medium can provide sufficient nutrients. Accordingly, the growth media provided to subsequent cultures may comprise growth factors combined with a basal medium and/or minimal essential medium. The growth media provided to subsequent cultures may include a balancing agent to buffer the media to a desired pH, such as, but not limited to, Earl's salts and/or HEPES.

If a culture includes fibroblasts, suitable growth factors may include, but are not limited to, L-glutamine, hydrocortisone hemisuccinate, linoleic acid, lecithin, serum albumin, basic fibroblasts growth factor, epidermal growth factor, transforming growth factor, insulin and/or vitamin C.

Growth of subsequent cultures with the first culture after seeding may be facilitated and/or enhanced by maintaining the cells of subsequent cultures in a proliferative phase. Cells of subsequent cultures may be maintained in a proliferative phase by growing the cells on a second surface to less than 100 percent confluence. For instance, growing the cells of subsequent cultures on second surface to approximately 80 to 90 percent confluence before seeding onto the surface of the co-culture may maintain the cells of the subsequent culture in a proliferative phase prior to seeding.

As to provide subsequent cultures a sufficient surface to become established, it may be necessary to provide areas on the surface free of preceding cultures. Providing such surfaces within a monolayer of established cultures may be accomplished by growing preceding cultures to a monolayer of less than 100% confluence and then creating voids in the monolayer of the preceding cultures by removing an appropriate amount of the monolayer. The amount removed will be dependent on the growth rate of cells together and/or the final cellular composition of the co-culture desired. For example, if a co-culture comprising two cell types is desired, and the second seeded cell type is sufficiently aggressively as to fill voids without allowing the first cells to significantly enter the voids, then approximately 50% of the monolayer of the first culture may be removed.

Voids may be created by removing portions of the monolayer of preceding cultures from the surface. For instance, voids may be created scraping or otherwise mechanically detaching portions of a previously cultured monolayer from the surface. It is also possible to remove portions of an established monolayer by first treating the monolayer with a detachment solution for a sufficient time to cause cells in the monolayer to begin to ball. Once the cells of the monolayer begin to ball, the detachment solution can be withdrawn and squirted back onto the monolayer to produce voids in the monolayer.

The serum collected from a co-culture of cells may be enhanced by maintaining the cells in a proliferative phase by growing the final co-culture to less than 100% confluence on the surface after over-seeding the final culture to be added. Maintaining the cells in a proliferative phase prior to and/or during serum collection may influence the composition of the serum. The composition of the serum may be adjusted by allowing at least a portion of the cells to senesce. Accordingly, the composition and/or ratio of senesced versus proliferative cells within the co-culture may influence the composition and/or quality of the serum collected. The quality of the serum may also be enhanced by stressing the cells within the co-culture. Cells within the co-culture may be stressed by selectively depriving the cells of at least one growth factor, nutrient and/or metabolic component. For example, cells within the co-culture may be stressed by depriving the cells of one or more growth factors while maintaining nutrient levels. Accordingly, production of a therapeutic serum may be induced in a co-culture by replacing the first growth media with a collection media lacking the growth factors of the first growth media, after the co-culture has grown to approximately 80 to 95% confluence. The co-culture may then be maintained for a period of time in the collection media sufficient to allow the co-culture to transform the collection media into a conditioned media comprising the therapeutic serum. After which, at least a portion of the conditioned medium containing the therapeutic serum may be collected.

As to facilitate further production of the therapeutic serum, the withdrawn portion of the conditioned medium may be replaced with fresh collection media. Production of the therapeutic serum may also be enhanced by allowing the co-culture to recover from the induced stress. Such a recovery phase may be provided by replacing the conditioned medium with fresh growth media containing the removed growth factors and allowing the culture to recover for a period of time. Depending on the cells included within the co-culture, a recovery period of approximately 24 to 72 hours may be sufficient.

After the therapeutic serum has been collected, a cosmetic preparation may be produced by adding the therapeutic serum to a cosmetically suitable base. The cosmetic base which may be used is not particularly limited and may include hydrogels, such as polyethylene glycol, oils, such as sunflower seed oil, sweet almond oil and/or coconut oil, and/or fats, such as Shea Butter. The cosmetic base may also include alcohols, polyols, emulsifiers, such as Ceteareth-20, carbomer and/or glycerol monostearate, preservatives, and/or moisturizers, such as hyaluronic acid. Antioxidants, such as vitamin E, vitamin A and/or vitamin C may also be included in the composition. The cosmetic preparation may include phytochemicals, such as resveritol, quercetin and/or epigallocatechin gallate. If desired, fragrances may also be added to the cosmetic preparation. The cosmetic preparation may contain other ingredients, such as pigments, flavoring agents, preservatives and/or sweeteners. The ingredients included within the cosmetic preparation are not particularly limited, as long as they collectively provide a cosmetically suitable preparation that is non-toxic when topically applied.

DETAILED DESCRIPTION

A method for obtaining a therapeutic serum suitable for inclusion in cosmetic preparation now will be described more fully with reference to specific examples. The serum, however, may be obtained in different manners, and thus should not be construed as limited to the specific examples provided. Accordingly, the serum may be obtained by a different ordering and/or sequence of the various steps and/or procedures detailed in the provided examples. For example, two or more steps may be performed concurrently or with partial concurrence. Also, some steps that are performed as discrete steps in the following examples may be combined, and steps being performed as a combined step may be separated into discrete steps, the sequence of certain steps may be reversed or otherwise varied, and the nature or number of discrete steps may be altered or varied. Accordingly, the provided examples are not intended to exclude any of such means of obtaining a therapeutic serum suitable for use in a cosmetic preparation.

Likewise, different reagents, techniques, materials and/or equipment other than those specifically mentioned may be utilized to provide the therapeutic serum.

A therapeutic serum suitable for inclusion in a cosmetic preparation may be produced by stressing a co-culture including proliferative cells. The co-culture of cells may be obtained by first establishing a monolayer of cells on a surface. After a monolayer of a first culture is established, a second culture comprising more resilient and/or aggressive cells may be seeded on the monolayer and established. Additional cultures comprising increasingly dominant cells may then be seeded and established until a monolayer the having the desired cellular composition is obtained. The monolayer is then stressed to obtain a serum by conditioning a collection medium. The obtained serum may be combined with a suitable cosmetic base to provide a cosmetic preparation.

For instance, a serum comprising Human Neonatal Fibroblast/Keratinocyte Conditioned Media may be obtained from a proliferative monolayer comprising a co-culture of keratinocytes and fibroblasts. The co-cultured monolayer may be established by first partially submerging a vial of frozen keratinocytes (obtained from LifeLine Cell Technologies) in a 37° C. water bath, without submerging the top of the vial. The vial is allowed to thaw in the water bath until a small piece of ice remains. The vial is then removed and sprayed with an ethanol solution. In a hood, keratinocytes are seeded from the vial at 2,500 to 5,000 cells per $cm^2$ onto a culture treated surface. The surface should be provided with an appropriate volume of a suitable growth media, such as a media including Basal DermaLife Media (LifeLine Cell Technologies) and growth factors comprising bovine pituitary extract, L-glutamine, hydrocortisone hemisuccinate, transforming growth factor, insulin, epinephrine and/or Apo-Transferrin. The seeded surface is then placed in an incubator and grown at 37° C. in the presence of humidified air comprising 5% $CO_2$. As to remove any residue DMSO and/or other solvents that may be present in the cryogenic solution, the growth media may be changed every 24 to 48 hours following initiation of the monoculture. After which time, the growth media may be changed every 48 to 72 hours.

Other means of obtaining the initial keratinocytes may also be employed. For instance, keratinocytes may be isolated from neonatal foreskin retrieved from circumcision using the techniques detailed in co-pending U.S. application Ser. No. 14/597,796, filed Jan. 15, 2015, the teachings of which are hereby incorporated by reference in their entirety.

The keratinocytes are allowed to grow in the growth media until 80-90% confluence is achieved. Voids are then created within the established monolayer by removing the growth media and washing twice with an appropriate volume of a buffer solution, such as phosphate buffer solution without calcium or magnesium. After washing with buffer solution, a sufficient volume of an enzymatic cell detachment solution to promote detachment of the cells from the surface is added. For instance, detachment of the cells may be promoted by adding 1 ml of HyQTase Solution, manufactured by HyClone Laboratories, Inc, per 25 cm$^2$ of growth area. The enzymatically treated monolayer may then be incubated at 37° C. until the keratinocytes start balling. The surface is then tilted to collect the enzyme solution with a pipette. The collected solution is sprayed at focused points onto the monolayer to create voids in about 50% of the monolayer. The enzyme solution and detached keratinocytes are then removed. The remaining monolayer is provided with a sufficient volume of the growth media and returned to the incubator. For example, an amount of media providing 10 ml of media per 55 cm$^2$ of growth area may be sufficient.

Simultaneously, a monolayer of fibroblasts is cultured on a second surface by submerging a vial of frozen fibroblasts (obtained from LifeLine Cell Technologies) in a 37° C. water bath, without submerging the top of the vial. The vial is allowed to thaw in the water bath until a small piece of ice remains. The vial is then removed and sprayed with an ethanol solution. In a hood, fibroblasts are seeded from the vial at 2,500 to 5,000 cells per cm$^2$ on to a culture treated surface. The surface should be provided with an appropriate volume of a suitable growth media, such as a media including Basal DermaLife Media (LifeLine Cell Technologies) and growth factors comprising L-glutamine, hydrocortisone hemisuccinate, lineolic acid, licithin, human serum albumin, basic fibroblasts growth factor, epidermal growth factor, transforming growth factor, insulin and/or vitamin C. The seeded surface is then placed in an incubator and grown at 37° C. in the presence of humidified air comprising 5% $CO_2$. As to remove any residue DMSO and/or other solvents that may be present in the cryogenic solution, the growth media may be changed every 24 to 48 hours following initiation of the monoculture. After which time, the growth media may be changed every 48 to 72 hours.

Other means of obtaining the initial fibroblasts may also be employed. For instance, fibroblasts may be isolated from neonatal foreskin retrieved from circumcision using the techniques detailed in co-pending U.S. application Ser. No. 14/597,796.

When the fibroblast monolayer reaches approximately 80 to 90% confluence, the surface is transferred to a hood and the growth media removed. The fibroblasts monolayer is then washed with a buffer solution, such as phosphate buffer solution without calcium or magnesium. A sufficient volume of a cell detachment solution to promote detachment of the fibroblasts from the second surface is then added. For instance, detachment of the fibroblasts may be promoted by adding 1 ml of Accutase Cell Detachment Solution, manufactured by Innovative Cell Technologies, Inc, per 25 cm$^2$ of growth area. The fibroblast cells are then incubated in the cell detachment solution at 37° C. until all the cells have detached. A homogenous suspension of cells is then obtained by mixing and approximately 250 μl of the fibroblasts suspension is over-seeded onto the keratinocyte monolayer. The over-seeded keratinocyte monolayer is then returned to the incubator. The co-culture is then grown in the keratinocyte growth media until 80 to 95% confluence is achieved.

A monolayer of co-cultured cells may also be achieved by culturing keratinocytes in the keratinocyte growth media until approximately 50% confluence is achieved. The keratinocyte monolayer may then be over-seeded with the cultured fibroblasts suspension. For example, a co-culture in a T175 cm$^2$ flask would be overlayed with 1.5 ml of fibroblast suspension generated from a confluent T75 cm$^2$ flask of fibroblasts dissociated using 3 ml of Accutase. The over-seeded keratinocyte monolayer may then be cultured in the incubator until approximately 80 to 95% confluence is achieved.

The co-culture of cells may be stressed to provide a therapeutic serum suitable for use in a cosmetic preparation. Stressing the co-culture may be achieved by selectively removing nutrients, growth factors and/or other favorable conditions. The stress need not be severe. Accordingly, sufficient stress may be induced by removing all or a portion of the growth factors while maintaining nutrient levels. Growth factors may be removed by extracting the keratinocyte growth media from the surface and rinsing the co-culture monolayer twice with a sufficient volume of a buffer solution, such as phosphate buffer solution lacking calcium and magnesium. As to ensure all growth factors are removed, the co-culture may be incubated for a period of time in a collection medium that is added to the surface and then discarded prior to serum collection. For instance, growth factors may be removed prior to serum collection by adding approximately 5.0 ml of a collection medium per 55 cm$^2$ of growth area and incubating for approximately six hours.

The collection medium may comprise a minimum essential medium with Earl's salt and have the nutrients of the keratinocyte growth medium.

After removal of the growth factors, a sufficient volume of fresh collection medium is added, and the surface returned to the incubator for a sufficient period of time to produce a conditioned medium form the collection medium. For example, incubating the co-culture in approximately 10.0 ml of fresh collection media per 55 cm$^2$ of growth area for approximately 48 hours may be sufficient to produce a conditioned media from the collection media. After incubating for a sufficient period of time, approximately 50% of the collection media is removed and replaced with an approximately equal amount of fresh collection media. The co-culture is then incubated for approximately 48 hours to produce more conditioned media. After which time, all of the conditioned media is removed.

The co-culture is then allowed to recover by removing the stress and incubating for a period of time. For instance, incubating in the presence of approximately 10.0 ml per 55 cm$^2$ of growth area of the keratinocyte growth media for approximately 24 to 72 hours may provide sufficient recovery. During recovery, the co-culture may be refreshed by seeding fresh cells of one or more of the cultures onto the monolayer.

After recovering, serum collection is repeated.

The process of the serum collection and recovery may be repeated until the co-cultures no longer produce serum of the desired quality. The quality of serum may begin to degrade when one or more of the cultures used to initially establish the co-culture reach 80% of their life expectancy as defined by the maximum number of population doublings.

The conditioned medium collected may be filtered using a suitable filter, such as a 0.45 μm Millipore filter. The serum collected from filtering the conditioned medium may be tested for sterility, virology and/or stability factors.

The therapeutic serum collected may be combined with a suitable cosmetic base as to provide therapeutic cosmetic preparation useful as a recovery cream, moisturizer, neck cream, eye cream and/or facial cream. After combining the therapeutic serum to the base, antioxidants, and/or fragrances may be added to the cosmetic preparation. The cosmetic preparation may comprise approximately 58 to 77 percent by mass of base, approximately 2 to 5 percent by mass of a moisturizer, approximately 9 to 33 percent by mass of the serum, 3 to 14 percent by mass of antioxidants, and approximately 0 to 0.01 percent by mass of fragrance. Other amounts and/or ingredients collectively providing a cosmetically suitable preparation may be utilized in combination with the serum.

In an exemplary embodiment, a facial cream cosmetic preparation may be prepared by adding 2.35 mass percent super low molecular weight hyaluronic acid added to 58.92 mass percent base. The base and hyaluronic acid combination may then be slowly mixed until homogenous. After which, 29.45 mass percent serum may be added to the base and hyaluronic acid mixture and slowly mixed until a homogenous mixture is obtained. Then 5.89 mass percent vitamin C may be slowly mixed in to provide a homogenous mixture. After providing a homogenous mixture including vitamin C, 2.94 mass percent vitamin E may be slowly mixed in to provide a homogenous mixture. Then 0.44 mass percent vitamin A may be mixed in to provide a final homogenous vitamin-base-moisturizer-serum composition. To this composition, 0.01 mass percent fragrance may be mixed in to provide a final homogenous cosmetic preparation.

In an exemplary embodiment, an eye cream cosmetic preparation may be prepared by combining 61.83 mass percent base with 30.90 mass percent serum and slowly mixing until a homogenous mixture of base and serum is obtained. To this mixture, 3.707 mass percent super low molecular weight hyaluronic acid may be slowly mixed in to provide a homogenous mixture. Then, 3.09 mass percent vitamin E may be slowly mixed in to provide another homogenous mixture. To this mixture, 0.463 mass percent vitamin A may be slowly mixed in to provide a homogenous vitamin-base-moisturizer-serum composition. To this composition, 0.01 mass percent fragrance may be slowly mixed in to provide a final homogenous cosmetic preparation.

In an exemplary embodiment, a neck cream cosmetic preparation may be prepared by combining 67.243 mass percent base with 16.810 mass percent serum, and mixing slowly to provide a homogenous mixture of base and serum. To this mixture 4.203 mass percent super low molecular weight hyaluronic acid may be slowly mixed in to provide a homogenous mixture. Then, 7.985 mass percent vitamin C may be slowly mixed in to provide a homogenous mixture. To this homogenous mixture, 3.329 mass percent vitamin E may be slowly mixed in to provide another homogenous mixture. After which, 0.42 mass percent vitamin A may be slowly mixed in to provide a homogenous vitamin-base-moisturizer-serum composition. To this composition, 0.01 mass percent fragrance may be mixed in to provide a final homogenous cosmetic preparation.

In an exemplary embodiment, a moisturizer cream cosmetic preparation may be prepared by combining 76.100 mass percent base with 9.605 mass percent serum and mixing slowly until a homogenous base-serum mixture is obtained. To this mixture, 3.42 mass percent super low molecular weight hyaluronic acid may be slowly mixed to provide another homogenous mixture. To this mixture, 6.60 mass percent vitamin C may be slowly mixed in to provide a homogenous mixture. After which, 3.805 mass percent vitamin E may be slowly mixed in to provide a homogenous mixture. Then, 0.46 mass percent vitamin A may be slowly mixed in to provide a homogenous vitamin-base-serum-moisturizer composition. To this composition, 0.01 mass percent fragrance may be mixed in to provide a cosmetic preparation.

In an exemplary embodiment, a recovery cream cosmetic preparation may be prepared by combining 66.67 mass percent base with 33.33 mass percent serum and mixing slowly until homogenous.

While the present invention has been described herein with respect to the exemplary embodiments, it will become apparent to one of ordinary skill in the art that many modifications, improvements and sub-combinations of the various embodiments, adaptations and variations can be made to the invention without departing from the spirit and scope thereof.

What is claimed:

1. A method of producing a serum, comprising the steps of:
   a) seeding a first surface with a first culture of cells;
   b) providing the first culture with a first growth medium comprising nutrients and at least one growth factor;
   c) growing the first culture to a monolayer of less than 100% confluence;
   d) over-seeding a second culture onto the first surface and the monolayer made in step (c), said second culture comprising cells more dominant than those in the first culture;
   e) growing the first and second cultures to less than 100% confluence in the presence of the first growth medium;
   f) after growing the first and second cultures to less than 100% confluence, replacing the first growth medium with a collection medium, said collection medium lacking at least one of the growth factors of the first growth medium;
   g) maintaining the first and second cultures for a period of time in the presence of the collection medium to produce a conditioned medium; and
   h) collecting at least a portion of the conditioned medium after the period of time, wherein said conditioned medium is a therapeutic serum.

2. The method of claim 1, further comprising growing the second culture on a second surface to less than 100% confluence before over-seeding onto the first surface.

3. The method of claim 1, wherein the second culture is grown in the presence of a second growth medium before over-seeding onto the first surface, said second growth medium comprising nutrients and at least one growth factor.

4. The method of claim 3, wherein the nutrients of the second growth media are provided by a basal medium.

5. The method of claim 3, wherein the growth factors of the second growth medium comprise at least one selected from the group consisting of L-glutamine, hydrocortisone hemisuccinate, lineolic acid, lecithin, human serum albumin, basic fibroblast growth factor, epidermal growth factor, transforming growth factor, insulin, and vitamin C.

6. The method of claim 1, wherein the nutrients of the first growth media are provided by a basal medium.

7. The method of claim 1, wherein the growth factors of the first growth medium comprise at least one selected from the group consisting of bovine pituitary extract, L-glutamine, hydrocortisone hemisuccinate, transforming growth factor, insulin, epinephrine, and ApoTransferrin.

8. The method of claim 1, wherein the collection medium comprises the nutrients of the first growth medium.

9. The method of claim 1, further comprising: after collecting at least a portion of the conditioned medium, replacing the conditioned medium with the first growth medium; and culturing the first culture and second culture in the first growth medium for a recovery period of time.

10. The method of claim 1, further comprising: before over-seeding the second culture onto the first surface, growing the first culture to a monolayer of approximately 80 to 90% confluence; and creating voids in the monolayer of the first culture.

\* \* \* \* \*